United States Patent [19]
Moore

[11] Patent Number: 5,286,633
[45] Date of Patent: Feb. 15, 1994

[54] ENZYMATIC TRIGLYCERIDE CONVERSION

[75] Inventor: Harry Moore, Oakley, Great Britain

[73] Assignee: Van den Bergh Foods Co., Division of Conopco, Inc., Lisle, Ill.

[21] Appl. No.: 900,227

[22] Filed: Jun. 17, 1992

[30] Foreign Application Priority Data

Jun. 18, 1991 [EP] European Pat. Off. .......... 91305516

[51] Int. Cl.$^5$ .............................................. C12P 7/64
[52] U.S. Cl. .................................... 435/134; 435/271
[58] Field of Search ............................ 435/134, 271

[56] References Cited

U.S. PATENT DOCUMENTS 4,420,560  12/1983  Matsuo et al. .

FOREIGN PATENT DOCUMENTS 0079986   6/1983   European Pat. Off. .
62-155048 12/1985  Japan .
1577933  10/1980   United Kingdom .
88/02775  6/1988   World Int. Prop. O. .
91/08676  6/1991   World Int. Prop. O. .

OTHER PUBLICATIONS

Chemical Abstract 94011F.
A. R. Macrae, J.A.O.C.S., 60 (2), 1983, pp. 291–294.
A. R. Macrae, Biocatalysts in Org. Synth., Proc. of Intern. Symp. Noordwijkerhout, Holland, Apr. 1985, pp. 195–208.
A. J. Russell and A. M. Klibanov, Biochem. Soc. Trans. vol. 17(1989) p. 1145.
F. X. Malcata c.s., J.A.O.C.S., 67 (12), 1990, pp. 890–910 European Search Report.

*Primary Examiner*—Herbert J. Lilling
*Attorney, Agent, or Firm*—Rimma Mitelman

[57] ABSTRACT

The invention is concerned with enzymic triglyceride conversions, wherein more than one enzymic conversion zone and preferably the same number of deacidifications units are applied. The fresh triglyceride feed stock and the compound providing fresh fatty acid moiety are introduced into different parts of the system so that fresh triglyceride is contacted with a mixture of the compound providing fatty acid moiety that is reduced in the amount of fatty acid moiety that should be introduced into the triglyceride.

10 Claims, 2 Drawing Sheets

ENZYMATIC TRIGLYCERIDE CONVERSION

BACKGROUND OF THE INVENTION

Since the first publication about enzymic interesterification (see e.g. GB 1,577,933) of triglyceride-containing systems in the presence of minimal amounts of water (i.e. amounts of water that are sufficient to activate the enzyme but that are so small that only very limited amounts of hydrolysis products and/or isomerized components derived from these products are formed), many publications have appeared, both in open literature and in patent literature (see e.g. A. R. Macrae, J.A.O.C.S., 60 (2), 1983, pages 291–294; A. R. Macrae, Biocatalysts in Org. Synth., Proc. of Intern. Symp. Noordwijkerhout, Holland, Apr. 1985, pages 195–208; A. J. Russell and A. M. Klibanov, Biochem. Soc. Transactions, Vol. 17 (1989), page 1145; F. X. Malcata c.s., J.A.O.C.S., 67 (12), 1990, pages 890–910; U.S. Pat. No. 4,420,560; JP 62-155048; WO 8802775, including the references cited), which discuss the enzymic modification of edible fats. According to this literature, the interesterification of blends of triglycerides can be carried out, as can the interesterification of blends of oils, with added free fatty acids or esters in order to effect an interchange of the acids originally present in the triglycerides with the added acid. For example, triolein can be enzymically reacted with stearic acid to produce a triglyceride rich in StOSt, which is a major component of cocoa butter. However, in order to produce high conversions of triolein into StOSt, large amounts of expensive stearic acid should be used relative to triolein and the acid by-product produced in the overall process has little volume.

Thus, although the knowledge and understanding of this particular art have greatly improved since the above-mentioned first publication, one main problem still remained, i.e. how to arrive at a process that minimizes the use of expensive acids (or derivatives thereof) and by which high conversion into the desired end products can still be achieved.

SUMMARY OF THE INVENTION

We have found a new process with which the above-mentioned purposes can be achieved. Therefore, our invention concerns an enzymic interesterification process in which the amount of acids (or derivatives thereof such as esters) required for the conversion is limited to a minimum while still giving high conversion rates.

Therefore, our process concerns enzymic interesterifications of triglyceride mixtures (=TG) and a compound providing fatty acid moieties (=FA) in a multi-step process, which process is performed in such a way that fresh triglyceride mixture (=TG) is contacted with partly converted fatty acid moiety mixture and partly converted triglyceride mixture is contacted with fresh fatty acid moiety mixture (=FA).

A suitable way to carry out the process is by applying two enzymic conversion zones, ECZ-1 and ECZ-2, wherein fresh TG is converted in ECZ-1 with a partly converted stream of a compound providing fatty acid moieties obtained in a deacidification unit (=DAU-1), while simultaneously, in ECZ-2, a fresh compound providing fatty acid moieties (=FA) is converted with partly converted triglycerides, also obtained in DAU-1, whereas the crude reaction products from the enzymic conversion zones ECZ-1 and ECZ-2 are led to deacidification unit DAU-1, wherein the crude mixture is separated into:

1) the partly converted TG, which is recycled to ECZ-2;
2) the partly converted compound providing fatty acid moieties, which is recycled to ECZ-1 and
3) the product triglyceride fraction.

However, our new process preferably concerns enzymic interesterifications of triglyceride mixtures (=TG) and compounds providing fatty acid moiety (=FA) in a multistep process wherein n-enzymic conversion zones and n-deacidification units are applied, in which process TG or partially converted TG are contacted with fresh FA or with FA mixtures wherein partially converted TG are formed enzymatically in each individual enzymic conversion zone (1 to n) from partially converted and deacidified TG obtained in a deacidification unit which is (at least) one number lower than the enzymic conversion zone, whereas the compound providing the fatty acid moiety (FA) that is led to each individual enzymic conversion zone is obtained in a deacidification unit that is (at least) one number higher than the enzymic conversion zone and crude reaction mixture of each enzymic conversion zone is led to the deacidification unit with the same ranking, while fresh TG is led to the first enzymic conversion zone; fresh FA is led to the last enzymic conversion zone; material containing waste fatty acid moiety is discarded from the first deacidification unit and product (=converted) TG is removed from the last deacidification unit.

The above-mentioned processes therefore imply that a gradual increase in converted triglycerides is obtained in a multi-step system, in which intermediate reaction products gradually enriched in desired reaction product are contacted with compounds providing acid moiety with an increased concentration of the acid moiety that has to be introduced into the TG.

The above-mentioned processes offer a more economical use of the compound providing acid moiety, resulting in a lower consumption of this compound, while the conversion rate is the same as for the conventional processes, or, alternatively, the same acid usage leads to a higher production of the desired triglycerides.

The number of reaction steps in our preferred process (so the number of enzymic conversion zones and deacidification zones) is, in principle, unlimited. In practice, we prefer using 2–3 reaction zones and 2–3 deacidification units.

In order to explain our invention further, we will now describe the process in a system with 3 reaction zones and 3 deacidification units, as represented in our FIGS. (=FIG. 1).

DETAILED DESCRIPTION OF THE INVENTION

Three enzymic conversion zones, ECZ (1) - ECZ (3), and three deacidification units, DAU (1) - DAU (3) are used.

The fresh triglyceride mixture is led to ECZ (1) by line (4) and contacted with enzyme together with compound providing fatty acid moiety introduced via line (9) that is obtained from DAU (2).

The crude reaction mixture (CRM) from ECZ (1) is led by line (5) to DAU (1). In DAU (1), this mixture is separated (in a conventional way, e.g. by steam distillation) into a waste FA stream, which is discarded by line (6) and a partially converted TG, which is transported from DAU (1) to ECZ (2) by line (7).

In ECZ (2), this product is contacted with enzyme and an FA stream (12) obtained from DAU (3).

The crude reaction mixture from ECZ (2) is transferred to DAU (2) by line (8) and separated in DAU (2) (conventionally) into an FA stream, which is led to ECZ (1) through line (9), as described above, and into a partially converted TG, which is led through line (10) to ECZ (3).

In ECZ (3), the partially converted TG is further converted by contact with enzyme and the compound providing fresh fatty acid moiety (line 13). The crude reaction mixture is transferred to DAU (3) by line (11) and separated (conventionally) into the desired TG product (by line 14) and into an FA stream, which is led to ECZ (2) by line (12).

Therefore, in the above-mentioned process the concentration of the desired TG components in the TG streams is increasing from ECZ (1) to ECZ (3) while the concentration of fatty acid moiety that should be introduced into the FA streams that are led to the EC zones, is reducing from ECZ (3) to ECZ (1).

Figure 3:
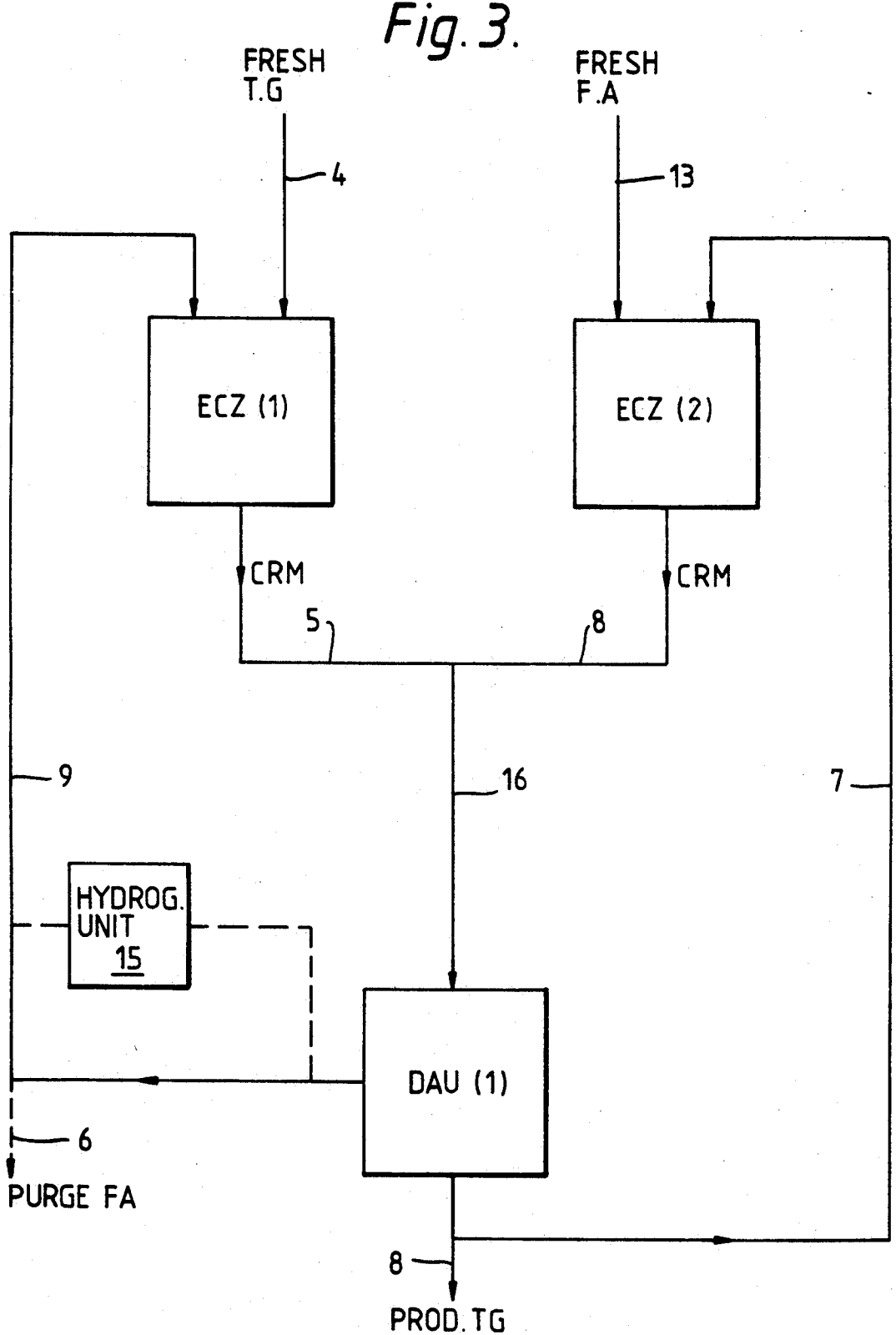
FIG. 3 depicts an alternate embodiment of the process according to the invention in which two enzymic conversion zones and one deacidification unit are employed.

An alternative embodiment of our invention is illustrated in FIG. 3. According to this process, two enzymic conversion zones (i.e. ECZ-1 and ECZ-2) are applied, whereas only one deacidification unit (=DAU-1) is used.

In ECZ-1, fresh TG are introduced (via line 4). The triglycerides are converted in the presence of an enzyme with a stream (9) containing a partly converted compound providing fatty acid moieties. Simultaneously, fresh compound providing fatty acid moieties is introduced via line (13) into ECZ-2 and contacted with partly converted triglycerides introduced via line (7), in the presence of an enzyme.

The crude reaction mixtures from ECZ-1 and ECZ-2 are removed via lines (5) and (8) and introduced into deacidification unit (1). In DAU-I, the mixture is separated into : partly converted TG, which is recycled via line (7) to ECZ-2; partly converted fatty acid moieties mixture, which is recycled via line (9) to ECZ-1 and product TG that is removed via line (8).

In cases appropriate, the partly converted fatty acid moiety mixture in line (9) can be hydrogenated in unit (15). Purge (6) can be applied to remove part of the spent mixture of fatty acid moieties.

In principle, our process can be applied for the preparation of any kind of (symmetrical) triglyceride. Thus, e.g., it is possible to prepare StOSt from 000 and stearic acid; to prepare OPO from PPP and oleic acid; to prepare St lin St from 0 Lin St and stearic acid, or StPSt from PPP and stearic acid. It is, of course, also possible to use a mixture of, e.g., acids, such as a mixture of stearic acid and palmitic acid in order to introduce St and P simultaneously into the triglyceride.

In this way it is possible to prepare hardstocks for margarines, such as INES fats (see e.g. our Australian Patent Application 549,465).

The starting triglyceride material that is used in our process can be any material, so it can be from vegetable but also from animal origin. However, preferred starting materials are oils or fats comprising mainly either $O_3$-type or $S_3$-type triglycerides, wherein O=unsaturated fatty acid with $\geq 18$ C-atoms and S=saturated fatty acids with at least 4 C-atoms.

The compound providing fatty acid moiety can be selected from free fatty acids, derivatives thereof that provide fatty acid moieties, such as esters or anhydrides. Preferred are saturated fatty acids or their lower alkyl esters (so $C_1$-$C_5$ alkyl groups) with $\geq 12$ C-atoms in the acid chain, if TG is of the $O_3$-type and unsaturated fatty acids or their lower alkyl esters ($C_1$-$C_5$ alkyl) with $\geq 16$ C-atoms in the acid chain, if TG is of the $S_3$-type.

Although all enzymes with interesterification activity can be used, we prefer using 1.3-specific enzymes, in particular 1.3-specific lipases. These enzymes can be natural enzymes but can also be obtained by genetic engineering.

The best results are obtained when the conversion is performed in such a way that the residence time in each enzymic conversion zone ensures a conversion to at least 75% of the theoretical equilibrium composition for that zone.

The product obtained will contain some mono- and diglyceride. It is advantageous to remove these components by performing a treatment of the end product by an enzyme specific for the hydrolysis of diglycerides and/or monoglycerides.

An improved product can also be obtained when any intermediate, partially converted TG, obtained in any deacidification unit is treated with an enzyme specific for diglyceride and/or monoglyceride hydrolysis.

In a further embodiment of the process according to the invention, the acid stream, discarded via line (6) and consisting mainly of oleic acid in case $O_3$ was the starting TG, can be hydrogenated in order to provide stearic acid, which can be used as a source for the stearic acid and thus be introduced via line (13). The hydrogenation can also be performed on the intermediate acid stream (12) and (9); however, the most effective way is to hydrogenate the stream in line (6).

EXAMPLE

Figure 1:
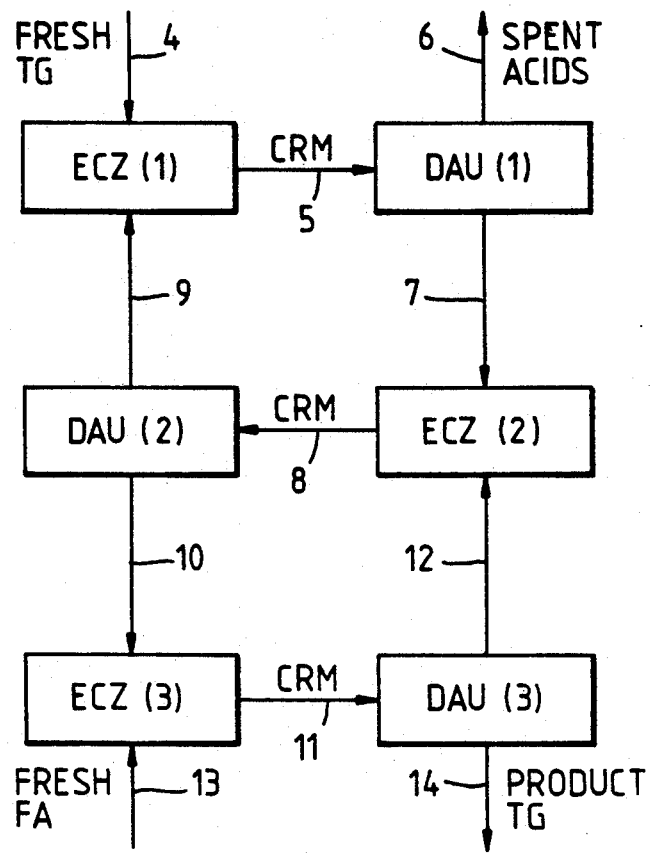
FIG. 1 depicts a process according to the invention in which three enzymic interstesterification zones and three deacidification units are employed.
Figure 2:
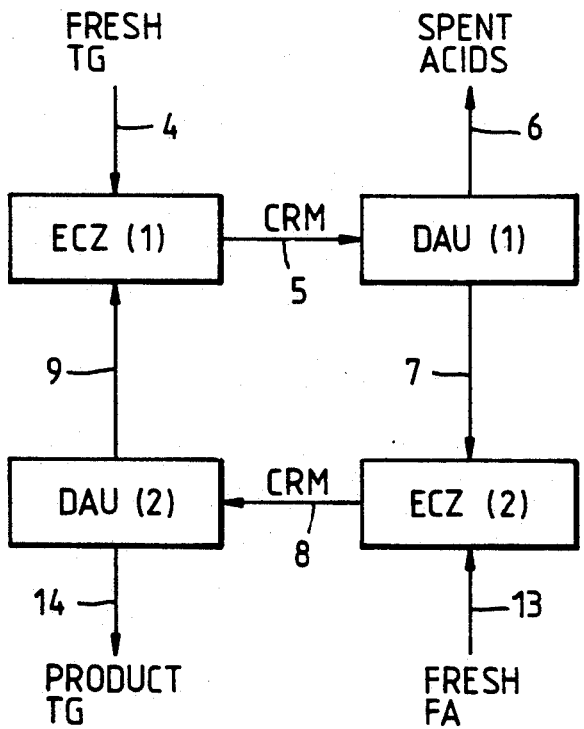
FIG. 2 depicts an alternate embodiment of the process according to the invention, as described in the Example.

A two-stage process is now described as represented in FIG. 2. A high-oleate sunflower oil is passed into ECZ(1) via line 4 together with the acids from DAU(2) in line (9). The product of ECZ(1) is pressed through line (5) to DAU(1). Line (6) contains the acids spent. The triglycerides in line (7) are passed to ECZ(2) to be reacted with the fresh stearic acid in line (13). The weight ratio of flows of fresh oil via line (4) to fresh acid via line (13) is 1.0 : 1.0. The enzymic product in line (8) is deacidified to yield acids via line (9) and a triglyceride product via line (14), which can be fractionated, if desired.

The composition of the triglycerides in the various lines is as follows :

| Line | SSS | SUS | SSU | SUU | Others |
| --- | --- | --- | --- | --- | --- |
| 4 | 0.0 | 1.3 | 0.2 | 20.2 | 78.3 |

-continued

| Line | SSS | SUS | SSU | SUU | Others |
|---|---|---|---|---|---|
| 5 | 0.5 | 29.0 | 0.7 | 49.1 | 20.7 |
| 7 | 0.5 | 29.0 | 0.7 | 49.1 | 20.7 |
| 8 | 2.5 | 62.6 | 1.3 | 29.8 | 3.8 |
| 14 | 3.0 | 61.6 | 1.8 | 29.8 | 3.8 |

Where S stands for saturated (palmitic or stearic) acid and U stands for unsaturated.

The acids in the various lines have the following composition :

| line | % S | % U |
|---|---|---|
| 13 | 99 | 1.0 |
| 8 | 81 | 19 |
| 9 | 81 | 19 |
| 5 | 54.5 | 45.5 |
| 6 | 54.5 | 45.5 |

I claim:

1. A process for the enzymic interesterification of a triglyceride and a compound providing a free fatty acid moiety, which process comprises the following steps:
   1) reacting in the presence of an enzyme in a first enzymic conversion zone (ECZ(1)) a mixture of:
      a) a starting triglyceride, and
      b) a compound providing a fatty acid moiety which compound has been partially converted, to obtain a first crude reaction mixture;
   2) reacting in the presence of an enzyme simultaneously with step (1), in a second enzymic conversion zone (ECZ(2)) a mixture of:
      c) a starting compound providing fatty acid moieties; and
      d) a partially converted triglyceride, to obtain a second crude reaction mixture;
   3) combining the first and the second crude reaction mixtures and to obtain a combined stream;
   4) separating the combined stream in a deacidification unit (DAU(1)) into:
      e) the compound providing a fatty acid moiety which compound has been partially converted;
      f) the partially converted triglyceride;
      g) a triglyceride product stream;
   5) recycling the compound providing a fatty acid moiety which compound has been partially converted to the first enzymic conversion zone (ECZ (1)); and
   6) recycling the partially converted triglyceride to the second enzymic conversion zone (ECZ(2)).

2. A process for the enzymic interesterification of a triglyceride and a compound providing a free fatty acid moiety, wherein several enzymic conversion zones are applied, which process comprises the following steps:
   1) reacting in the presence of an enzyme in a first enzymic conversion zone (ECZ(1)) a mixture of:
      a) a starting triglyceride and
      b) a compound providing a fatty acid moiety which compound has been partially converted, to obtain a first crude reaction mixture;
   2) reacting in the presence of an enzyme, simultaneously with steps (1), in a second enzymic conversion zone (ECZ(2)) a mixture of:
      c) a starting compound, providing a fatty acid moiety and
      d) a partially converted triglyceride, to obtain a second crude reaction mixture;
   3) separating the first crude reaction mixture in a first deacidification unit (DAU(1)) into:
      e) spent acids and
      f) the partially converted triglyceride;
   4) separating the second crude reaction mixture in a second deacidification unit (DAU(2)) into:
      g) a triglyceride product stream and
      h) the compound providing a fatty acid moiety which compound has been partially converted;
   5) recycling the compound a fatty acid moiety which compound has been partially converted to the first enzymic conversion zone (ECZ(1)); and
   6) recycling the partially converted triglyceride to the second enzymic conversion zone (ECZ(2)).

3. A process for the enzymic interesterification of a triglyceride and a compound providing a fatty acid moiety, wherein several enzymic conversion zones are applied, which process comprises the following steps:
   1) reacting in the presence of an enzyme in a first enzymic conversion zone (ECZ(1)) a mixture of:
      a) a starting trigylceride and
      b) a compound providing a fatty acid moiety which compound has been partially converted, to obtain a first crude reaction mixture;
   2) reacting in the presence of an enzyme, simultaneously with step (1), in a second enzymic conversion zone (ECZ(2)) a mixture of:
      c) a partially converted triglyceride, and
      d) a compound providing a fatty acid moiety which compound has been converted to a lesser extent than the compound (b) in step 1);
   3) reacting in the presence of an enzyme, simultaneously with steps (1) and (2) in a third enzymic conversion zone (ECZ(3)) a mixture of:
      e) a starting compound providing a fatty acid moiety and
      f) a triglyceride which has been converted to a larger extent than compound (c) in step (2) to obtain a third crude reaction mixture;
   (4) separating the first crude reaction mixture in a first deacidification unit (DAU(1)) into:
      g) spent acids and
      h) the partially converted triglyceride;
   5) separating the second crude reaction mixture in a second deacidification unit (DAU(2)) into:
      i) the compound providing a fatty acid moiety which compound has been partially converted;
      j) the compound (f) of step (3);
   6) separating the third crude reaction mixture in a third deacidification unit (DAU(3)) into:
      k) a triglyceride product stream and
      l) the compound (d) of step (2);
   7) recycling the partially converted triglyceride obtained in step (4h) to the second enzymic conversion zone (ECZ(2));
   8) recycling the compound obtained in step (5i) to the first enzymic conversion zone (ECZ (1));
   9) recycling the compound obtained in step (5j) to the third enzymic conversion zone (ECZ (3)); and
   10) recycling the compound obtained in step (6l) to the second enzymic conversion zone (ECZ(2)).

4. Process according to claim 1, wherein the number of zones and the number of units is 2–3.

5. Process according to claim 1, wherein the starting triglyceride material comprises predominantly O3-type or mainly S3-type triglycerides (O=unsaturated fatty acids with $\geq 18$ C-atoms; S=saturated fatty acids with $\geq 16$ C-atoms).

6. Process according to claim 1, wherein the compound providing fatty acid moiety is selected from:
   a) saturated fatty acids or their lower alkyl esters with $\geq$ 12 C-atoms in the acid chain if TG is of the $O_3$-type;
   b) unsaturated fatty acids or their lower alkyl esters with $\geq$ 16 C-atoms in the acid chain if TG is of the $S_3$-type.

7. Process according to claim 1, wherein the enzyme is a 1.3-specific enzyme.

8. Process according to claim 1, wherein residence time in each enzymic conversion zone is such that conversion to at least 75% of the theoretical equilibrium composition for that zone is obtained.

9. Process according to claim 1 wherein the converted TG product is treated with an enzyme specific for the hydrolysis of diglycerides.

10. Process according to claim 1, wherein any intermediate, partially converted triglyceride obtained in any deacidification unit, is treated with an enzyme specific for diglyceride hydrolysis.

* * * * *